US011957666B2

(12) United States Patent
Polvino

(10) Patent No.: US 11,957,666 B2
(45) Date of Patent: *Apr. 16, 2024

(54) REGIMEN FOR SUPPRESSING ORGAN REJECTION

(71) Applicant: Veloxis Pharmaceuticals, Inc., Cary, NC (US)

(72) Inventor: William J. Polvino, Edison, NJ (US)

(73) Assignee: VELOXIS PHARMACEUTICALS, INC., Cary, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/447,581

(22) Filed: Sep. 14, 2021

(65) Prior Publication Data

US 2022/0249449 A1 Aug. 11, 2022

Related U.S. Application Data

(63) Continuation of application No. 16/678,527, filed on Nov. 8, 2019, now Pat. No. 11,141,408, which is a continuation of application No. 15/682,275, filed on Aug. 21, 2017, now Pat. No. 10,485,793, which is a continuation of application No. 14/867,773, filed on Sep. 28, 2015, now Pat. No. 9,775,834, which is a continuation of application No. 14/317,500, filed on Jun. 27, 2014, now Pat. No. 9,168,246.

(60) Provisional application No. 61/840,354, filed on Jun. 27, 2013.

(51) Int. Cl.
| | |
|---|---|
| *A61K 31/435* | (2006.01) |
| *A61K 9/00* | (2006.01) |
| *A61K 9/20* | (2006.01) |
| *A61K 31/436* | (2006.01) |
| *A61K 31/5377* | (2006.01) |
| *A61K 39/395* | (2006.01) |
| *A61K 45/06* | (2006.01) |
| *A61P 43/00* | (2006.01) |
| *A61K 39/00* | (2006.01) |

(52) U.S. Cl.
CPC .......... *A61K 31/436* (2013.01); *A61K 9/0053* (2013.01); *A61K 9/2013* (2013.01); *A61K 9/2018* (2013.01); *A61K 9/2031* (2013.01); *A61K 9/2036* (2013.01); *A61K 9/2054* (2013.01); *A61K 31/5377* (2013.01); *A61K 39/3955* (2013.01); *A61K 45/06* (2013.01); *A61P 43/00* (2018.01); *A61K 9/2077* (2013.01); *A61K 2039/505* (2013.01)

(58) Field of Classification Search
CPC .................................................. A61K 31/435
USPC ...................................................... 514/291
See application file for complete search history.

(56) References Cited

U.S. PATENT DOCUMENTS

| | | |
|---|---|---|
| 5,260,301 A | 11/1993 | Nakanishi et al. |
| 5,543,408 A | 8/1996 | Fu et al. |
| 5,665,727 A | 9/1997 | Grassberger et al. |
| 5,688,529 A | 11/1997 | Lidgate et al. |
| 6,346,537 B1 | 2/2002 | Hata et al. |
| 6,440,458 B1 | 8/2002 | Yamashita et al. |
| 7,994,214 B2 | 8/2011 | Holm |
| 8,591,946 B2 | 11/2013 | Holm |
| 8,664,239 B2 | 3/2014 | Gordon et al. |
| 8,685,998 B2 | 4/2014 | Gordon et al. |
| 9,168,246 B2 | 10/2015 | Polvino |
| 9,775,834 B2 | 10/2017 | Polvino |
| 10,485,793 B2 | 11/2019 | Polvino |
| 11,110,081 B2 * | 9/2021 | Gordon ................ A61K 31/436 |
| 11,141,408 B2 * | 10/2021 | Polvino ................ A61K 45/06 |
| 2006/0287352 A1 | 12/2006 | Holm et al. |
| 2010/0105717 A1 | 4/2010 | Gordon et al. |
| 2011/0201639 A1 | 8/2011 | Skak et al. |

FOREIGN PATENT DOCUMENTS

| | | |
|---|---|---|
| JP | 200837808 | 2/2008 |
| WO | WO-2005020993 A1 | 3/2005 |
| WO | WO-2005020994 A1 | 3/2005 |
| WO | WO-20080145143 A1 | 12/2008 |

(Continued)

OTHER PUBLICATIONS

MacPhee et al., "The Influence of Pharmacogenetics on the Time to Achieve Target Tacrolimus Concentrations after Kidney Transplantation", 2004, American Journal of Transplantation, 4(6), pp. 914-919. (doi: 10.1111/j.1600-6143.2004.00435.x) (Year: 2004).*
Passey et al., "Dosing equation for tacrolimus using genetic variants and clinical factors", 2011, British Journal of Clinical Pharmacology, 72(6), pp. 948-957. (DOI:10.1111/j.1365-2125.2011.04039.x) (Year: 2011).*
Lamba et al., "PharmGKB summary: very important pharmacogene information for CYP3A5", 2012, Pharmacogenetics and Genomics, 22(7), pp. 555-558. (DOI: 10.1097/FPC.0b013e328351d47f) (Year: 2012).*
Advagraf: EPAR Product Information, Nov. 28, 2013.
Astragraf XL Prescribing Information, Feb. 28, 2014.
Barraclough et al., *Drugs* 2011, 71(12):1561-1577.
Prograf Prescribing Information, Aug. 14, 2012.

(Continued)

*Primary Examiner* — Raymond J Henley, III
(74) *Attorney, Agent, or Firm* — Blank Rome LLP

(57) ABSTRACT

The present invention relates to a method of suppressing organ rejection in a patient receiving an organ transplant by initiating oral treatment with a once-daily extended release tacrolimus dosage form, for example, at an initial dose of from about 0.15 to about 0.20 mg/kg/day within 24 or 48 hours following transplantation. The once-daily extended release tacrolimus dosage form (i) provides low fluctuation and/or swing of tacrolimus, (ii) provides a significantly lower $C_{max}$ than an immediate release formulation of tacrolimus while providing the same or greater area under the curve (AUC), (iii) releases the tacrolimus substantially in the colon and/or the lower ileum, (iv) releases at most 63.5% of the tacrolimus in the dosage form at the 12 hour time point, or (v) any combination of any of the foregoing.

20 Claims, No Drawings

(56) References Cited

FOREIGN PATENT DOCUMENTS

| WO | WO-2010005980 A1 | 1/2010 |
| WO | WO-2011100975 A2 | 8/2011 |

OTHER PUBLICATIONS

Srinivas et al., *Am. J. Transplant* 2010; 10: 2571-2573.

Silva, et al., One-Year Results with Extended-Release Tacrolimus/MMF, Tacrolimus/MMF and Cyclosporine/MMF in De Novo Kidney Transplant Recipients, American Journal of Transplantation, 2007, 7:595-608.

Ho, et al., Once-Daily Extended-Release Versus Twice-Daily Standard-Release Tacrolimus in Kidney Transplant Recipients: A Systematic Review, Clinical and Translational Research, 2013, 95:9:1120-1128.

International Search Report issued in PCT/IB2014/062668 dated Oct. 15, 2014.

Chharbra, et al., Long-Term Kidney Allograt Function and Survival in Prednisone-Free Regiments: Tracrolimus/Mycophenolate Mofetil versus Tacrolimus/Sirolimus, Mar. 2012, Clin. J. Am. Soc. Nephrol., vol. 7, No. 3, pp. 504-512, Published online on Jan. 2012.

Bunnapradist, et al., LCPT Once-Daily Extended-Release Tacrolimus Tablets Versus Twice-daily Capsults: A Pooled Analysis of Two Phase 3 Trials in Importat de novo and Stable Kidney Transplant Recipient Subgroups, 2016, Transplant International, 29:5:603-611.

Li, et al., In Vitro Evaluation of Dissolution Behavior for a Colon-specific Drug Delivery System (CODESTM) in Multi-pH Media Using United States Pharmacopeia Apparatus II and III, 2002, AAPS PharmSciTech, 3(59), pp. 1-9, (https://doi.org.10.1208/pt030433 (Year: 2002).

O'Dwyer, et al., In Vitro Methods to Assess Drug Precipitation in the Fasted Small Intestine—a PEARRL review, 2019, Journal of Pharmacy and Pharmacology, 71(4), pp. 536-556. (Year 2019).

\* cited by examiner

REGIMEN FOR SUPPRESSING ORGAN REJECTION

This application is a continuation of U.S. patent application Ser. No. 16/678,527, filed Nov. 8, 2019, which is a continuation of U.S. patent application Ser. No. 15/682,275, filed Aug. 21, 2017, now U.S. Pat. No. 10,485,793, which is a continuation of U.S. patent application Ser. No. 14/867,773, filed Sep. 28, 2015, now U.S. Pat. No. 9,775,834, which is a continuation of U.S. patent application Ser. No. 14/317,500, filed Jun. 27, 2014, now U.S. Pat. No. 9,168,246, which claims priority to U.S. Provisional Application No. 61/840,354, filed Jun. 27, 2013, which is hereby incorporated by reference.

FIELD OF THE INVENTION

The present invention relates to a method of suppressing organ rejection in a patient receiving an organ transplant (e.g., a de novo kidney transplant recipient) by initiating oral treatment with a once-daily extended release tacrolimus dosage form, for example, at an initial dose of from about 0.15 to about 0.20 mg/kg/day, within 24 or 48 hours following transplantation. The once-daily extended release tacrolimus dosage form (i) provides low fluctuation and/or swing of tacrolimus, (ii) provides a significantly lower $C_{max}$ than an immediate release formulation of tacrolimus while providing the same or greater area under the curve (AUC), (iii) releases the tacrolimus substantially in the colon and/or the lower ileum, (iv) releases at most 63.5% of the tacrolimus in the dosage form at the 12 hour time point, or (v) any combination of any of the foregoing.

BACKGROUND OF THE INVENTION

Tacrolimus is a macrolide lactone also known as FK506, fugimycin or tsukubaenolide. Tacrolimus is marketed under the tradenames Prograf® and Advagraf® as an immunosuppressive agent to prevent allograft rejection, i.e. rejection of transplanted organs. In the U.S., Prografo® (NDA No. 050708) is approved for the prophylaxis of organ rejection in patients receiving allogeneic liver, kidney, or heart transplants Advagraf is a once-daily formulation which has not received approval in the U.S. Advagraf failed a non-inferiority study a few years ago as reported in Srinivas et al., *Am. J. Transplant* 2010; 10: 2571-2573. According to Srinivas, > Although, it has never been definitively determined whether calcineurin inhibitor (CNI) efficacy in general and tacrolimus efficacy in particular is best correlated with AUC, peak or trough, if the AUCs were similar in this study the obvious conclusion would be that the observed efficacy failure [of Advagraf] is most likely related to lower and less frequent peaks with the once a day formulation. Interestingly, in the other phase III trial with once a day tacrolimus, rejection rates were also higher compared to twice a day tacrolimus with equivalent trough levels throughout the study, a further indication that the lower and less frequent tacrolimus peak might be detrimental to efficacy Similarly, Barraclough et al., *Drugs* 2011, 71(12):1561-1577, reported:

> Although efficacy of tacrolimus has never been definitively associated with peak or trough concentrations or AUC, an association of peak ciclosporin concentrations with freedom from acute rejection has been demonstrated. This suggests the possibility that the higher rejection rates observed in the previously mentioned studies may be related to the lower and less frequent concentration peaks that are seen with the Advagraf® formulation.

WO 2005/020993, WO 2005/020994, WO 2008/0145143, WO 2010/005980, and WO 2011/100975 disclose tacrolimus-containing pharmaceutical compositions with improved bioavailability.

There is a continuing need for an improved once-daily tacrolimus regimen which has the same or better efficacy than twice-daily tacrolimus with fewer adverse events.

SUMMARY OF THE INVENTION

The present inventors have discovered that certain once-daily extended release dosage forms are particularly effective at suppressing early acute organ rejection (for example, in de novo transplant recipients). The extended release dosage form (i) provides low fluctuation and/or swing of tacrolimus (relative to, for example, Prograf and/or Advagraf), (ii) provides a significantly lower $C_{max}$ (e.g., at least 15% lower (e.g., 15-30% lower $C_{max}$) than an immediate release formulation of tacrolimus (such as Prograf) at the same dose while providing the same or greater area under the curve (AUC), (iii) releases the tacrolimus such that absorption of the tacrolimus takes place substantially in the colon (such as one or more locations of the colon ascendens, colon transversum and colon decendens) and/or the lower ileum, (iv) releases at most 63.5% of the tacrolimus in the dosage form at the 12 hour time point, or (v) any combination of any of the foregoing.

The extended release dosage forms permit a higher initial daily dose of tacrolimus to be administered to the transplant recipient (i.e., a transplant patient who has not previously received tacrolimus following the transplantion), without a significant increase in adverse events. Without being bound by any particular theory, it is theorized that the higher initial daily dose results in improved imunosuppression in the transplant recipient which in turn reduces the risk of acute rejection of the organ following transplantation. In one embodiment, the initial daily dose of tacrolimus is from about 0.15 to about 0.20 mg/kg, e.g., about 0.15, 0.16, 0.17, 0.18, 0.19, or 0.20 mg/kg. In a preferred embodiment, the initial daily dose of tacrolimus is about 0.17 mg/kg. In another embodiment, the transplant recipient has never previously been administered tacrolimus. In yet another embodiment, treatment with the extended release tacrolimus dosage form is initiated within 24 or 48 hours of receiving the organ transplant.

One embodiment of the present invention is a method of suppressing organ rejection in a recipient of a liver, kidney, or heart transplant (e.g., an allogeneic liver, kidney, or heart transplant). The method includes initiating oral treatment with a once-daily extended release tacrolimus dosage form of the present invention at an initial dose of from about 0.15 to about 0.20 mg/kg/day within 24 or 48 hours following transplantation. The extended release tacrolimus dosage form preferably has a lower fluctuation and/or swing than Prograf and/or Advagraf. For example, the extended release tacrolimus dosage form preferably has a fluctuation of less than 100%, a swing less than 120%, or both.

Another embodiment is a method of suppressing organ rejection in a de novo transplant recipient (e.g., a de novo kidney transplant patient) by (a) initiating oral treatment with a once-daily extended release tacrolimus dosage form as described herein at an initial dose of from about 0.15 to about 0.20 mg/kg within 24 or 48 hours following transplantation;

(b) concomitantly treating the recipient with an IL-2 receptor antagonist (such as basiliximab) and mycophenolate mofetil; and (c) adjusting the dose of the extended release tacrolimus dosage form so that the whole blood pre-dose (trough) concentration of tacrolimus is maintained in the range of from about 5 to about 20 ng/mL.

In one embodiment, step (c) includes adjusting the dose of the extended release tacrolimus dosage form so that the whole blood pre-dose (trough) concentration of tacrolimus is maintained in the range of from about 6 to about 11 ng/mL for the first 30 days, and from about 4 to about 11 ng/mL after 30 days. In another embodiment, step (c) includes adjusting the dose of the extended release tacrolimus dosage form so that the whole blood pre-dose (trough) concentration of tacrolimus is maintained in the range of from about 4 to about 11 ng/ml during the first 3 or 12 months post-transplant.

In another embodiment, 1 g of mycophenolate mofetil is administered twice daily (2 g daily dose).

In yet another embodiment, a first 20 mg dose of basiliximdab is administered 2 hours prior to transplantation, and a second 20 mg dose of basiliximdab is administered 4 days after transplantation.

Step (b) may further include also concomitantly treating the recipient with one or more corticosteroids, such as prednisone or an equivalent to it. In one embodiment, the recipient is maintained for the first month post-transplant on a minimum of 10 mg of prednisone or an equivalent to it per day and optionally a minimum of 5 mg of prednisone or an equivalent to it per day thereafter.

Yet another embodiment is a method of suppressing organ rejection in a de novo transplant recipient (e.g., a de novo kidney transplant patient) by (a) initiating oral treatment with a once-daily extended release tacrolimus dosage form as described herein at an initial dose of from about 0.15 to about 0.20 mg/kg within 24 hours following transplantation;

(b) concomitantly treating the recipient with azathioprine or other purine biosynthesis inhibitor; and (c) adjusting the dose of the extended release tacrolimus dosage form so that the whole blood pre-dose (trough) concentration of tacrolimus is maintained in the range of from about 5 to about 20 ng/mL. In one embodiment, step (c) includes adjusting the dose of the extended release tacrolimus dosage form so that the whole blood pre-dose (trough) concentration of tacrolimus is maintained in the range of from about 7 to about 20 ng/mL for the first 3 months, and from about 5 to about 15 ng/mL for the next 9 months.

Yet another embodiment is a method of reducing or minimizing the risk or incidence of complications due to organ transplantation (such as kidney transplantation) by performing any of the method steps discussed herein.

The method steps of the present invention also result in reduced incidence of complications of the transplanted organ (e.g., kidney), peripheral oedema, diarrhea, deep vein thrombosis (DVT), constipation, anemia, low blood phosphate, nausea, or any combination of any of the foregoing.

Yet another embodiment is a method of reducing or minimizing the risk or incidence of adverse events in a patient in need of tacrolimus (such as a transplant recipient) by performing any of the method steps discussed herein. The adverse events which can be reduced or minimized include complications of the transplanted organ (e.g., kidney), peripheral oedema, diarrhea, deep vein thrombosis (DVT), constipation, anemia, low blood phosphate, nausea, or any combination of any of the foregoing.

In any of the embodiments described above, the patient can be a kidney transplant patient such as a de novo kidney transplant patient.

Yet another embodiment is a method of suppressing organ rejection in a recipient of a liver transplant (e.g., an allogeneic liver transplant, a de novo liver transplant patient, or a de novo allogeneic liver transplant). The method includes initiating oral treatment with a once-daily extended release tacrolimus dosage form of the present invention at an initial dose of from about 0.15 to about 0.20 mg/kg/day, or a dose to provide and maintain a whole blood pre-dose (trough) concentration of tacrolimus in the range of from about 5 to about 20 ng/mL, within 24 or 48 hours following transplantation.

Yet another embodiment is a method of suppressing organ rejection in a recipient of an allogeneic heart transplant (e.g., an allogeneic heart transplant, a de novo heart transplant patient, or a de novo allogeneic heart transplant patient). The method includes initiating oral treatment with a once-daily extended release tacrolimus dosage form of the present invention at an initial dose of from about 0.15 to about 0.20 mg/kg/day, or a dose to provide and maintain a whole blood pre-dose (trough) concentration of tacrolimus in the range of from about 10 to about 20 ng/mL, within 24 or 48 hours following transplantation. In one embodiment, the method further includes adjusting the dose of the extended release tacrolimus dosage form so that the whole blood pre-dose (trough) concentration of tacrolimus is maintained in the range of from about 5 to about 20 ng/ml during the first 3 months, and in the range of from about 5 to about 15 ng/ml after.

The patient in any of the embodiments described above may suffer from, or have a history of, one or more of peripheral oedema, diarrhea, deep vein thrombosis, constipation, anemia, low blood phosphate, and nausea. The patient in any of the embodiments described above may be Caucasian or African-American. Furthermore, the transplant recipient in any of the embodiments described above can be an adult kidney transplant recipient, such as a de novo adult kidney transplant recipient.

DETAILED DESCRIPTION OF THE INVENTION

Definitions

As used herein, the term "bioequivalency" denotes a scientific basis on which generic and brand name drugs are compared with one another. For example, drugs are bioequivalent if they enter circulation at the same rate when given in similar doses under similar conditions. Parameters often used in bioequivalence studies are $t_{max}$, $C_{max}$, $AUC_{0\text{-}infinity}$, and $AUC_{0\text{-}t}$. Furthermore, in the present context, a dosage form is regarded as bioequivalent to Prograf® or a similar commercially available tacrolimus-containing product if the value of the parameter (e.g., $C_{max}$ and/or AUC) used is within 80-125% of that of Prograf® or the similar commercially available tacrolimus-containing product used in the test.

In the present context "$t_{max}$" denotes the time to reach the maximal plasma concentration ($C_{max}$) after administration. $AUC_{0\text{-}infinity}$ denotes the area under the plasma concentration versus time curve from time 0 to infinity. $AUC_{0\text{-}t}$ denotes the area under the plasma concentration versus time curve from time 0 to time t. MRT denotes mean residence time for tacrolimus. Swing denotes $(C_{max}-C_{min})/C_{min}$ and fluctuation denotes $(C_{max}-C_{min})/C_{average}$. Peak-trough fluctuation denotes $C_{max}/C_{min}$.

Unless otherwise specified, Prograf refers to the drug product approved by the U.S. Food and Drug Administration under New Drug Application (NDA) No. 050708.

Unless otherwise specified, Advagraf refers to the drug product approved by the European Medicines Agency under EMA Product No. EMEA/H/C/000712.

Dosage Regimen

In one embodiment, the initial daily dose of tacrolimus is from about 0.15 to about 0.20 mg/kg, e.g., about 0.15, 0.16, 0.17, 0.18, 0.19, or 0.20 mg/kg. In another embodiment, the initial daily dose of tacrolimus is about 0.17 mg/kg. In another embodiment, the transplant recipient has never previously been administered tacrolimus. In yet another embodiment, treatment with the extended release tacrolimus dosage form is initiated within 24 or 48 hours of receiving the organ transplant. In yet another embodiment, the patient is Caucasian.

Many African-American patients have more rapid clearance of tacrolimus (for example due to the expression of the Cyp 3A5® 1 genotype). As a result, the dose for African-American patients may be higher than those for other patients. For example, the dose for African-American patients may range from about 0.20 to about 0.30 mg/kg, such as from about 0.21 mg/kg to about 0.27 mg/kg.

The extended release oral dosage form may be administered in the morning or evening (e.g., at bedtime). In one embodiment, the dosage form is administered in the morning each day. In another embodiment, the dosage form is administered in the evening each day.

Another embodiment is a method of suppressing organ rejection in a de novo kidney transplant recipient by (a) initiating oral treatment with a once-daily extended release tacrolimus dosage form as described herein at an initial dose of from about 0.15 to about 0.20 mg/kg within 24 or 48 hours following transplantation;

(b) concomitantly treating the recipient with an IL-2 receptor antagonist (such as basiliximab) and mycophenolate mofetil; and (c) adjusting the dose of the extended release tacrolimus dosage form so that the whole blood pre-dose (trough) concentration of tacrolimus is maintained in the range of from about 5 to about 20 ng/mL.

In one embodiment, step (c) includes adjusting the dose of the extended release tacrolimus dosage form so that the whole blood pre-dose (trough) concentration of tacrolimus is maintained in the range of from about 6 to about 11 ng/mL for the first 30 days post-transplant, and from about 4 to about 11 ng/mL after 30 days.

In another embodiment, step (c) includes adjusting as necessary the dose of the extended release tacrolimus dosage form(s) so that the whole blood pre-dose (trough) concentration of tacrolimus is maintained in the range of from about 8.8 to about 9.3 ng/mL from day 2 to week 3 of tacrolimus treatment, and from about 6.5 to about 8.8 ng/mL for month 1 to 12.

In another embodiment, 1 g of mycophenolate mofetil is administered twice daily (2 g daily dose).

In yet another embodiment, a first 20 mg dose of basiliximdab is administered 2 hours prior to transplantation, and a second 20 mg dose of basiliximdab is administered 4 days after transplantation.

Step (b) may further include also concomitantly treating the recipient with one or more corticosteroids, such as prednisone or an equivalent to it. In one embodiment, the recipient is maintained for the first month post-transplant on a minimum of 10 mg of prednisone or an equivalent to it per day and optionally a minimum of 5 mg of prednisone or an equivalent to it per day thereafter.

In another embodiment, the patient's tacrolimus blood concentrations are maintained between about 7 and about 20 ng/ml. For example, the patient's tacrolimus blood concentrations can be maintained between about 7 and about 20 ng/ml for the first 3 months (months 1-3) (e.g., approximately 7 to 12 ng/ml at steady state, e.g., after 7 days of treatment), and between about 5 and about 15 ng/ml for the next 9 months (months 4-12) (e.g., approximately 7 to 12 ng/ml).

In yet another embodiment, the patient's tacrolimus blood trough concentrations are maintained between about 7 and about 20 ng/ml. For example, the patient's tacrolimus blood trough concentrations can be maintained between about 7 and about 20 ng/ml for the first 3 months (months 1-3) (e.g., approximately 7 to 12 ng/ml at steady state, e.g., after 7 days of treatment), and between about 5 and about 15 ng/ml for the next 9 months (months 4-12) (e.g., approximately 7 to 12 ng/ml).

Organ transplant patients can be converted from a different tacrolimus formulation, such as twice-daily Prograf, another immediate release formulation of tacrolimus, Advagraf, or a bioequivalent formulation to one of them, to the extended release dosage form of the present invention. Because the extended release dosage form may have improved bioavailability, the tacrolimus daily dose administered to a patient switching from Prograf or Advagraf can be lowered, e.g., at a ratio of about 0.66-0.80:1 such as about 0.7:1 (extended release dosage form to Prograf or Advagraf). In one embodiment, the conversion is to be performed at a dosage ratio of about 0.66-0.80:1 (according to the closest available tablet strength). In other words, for every 1 mg of Prograf® administered, only about 0.66 to about 0.80 mg of tacrolimus in the extended release oral dosage form is administered. For African-American patients switching, the dosage ratio can be about 0.85:1. In another embodiment, a patient is switched from Advagraf to the extended release dosage form of the present invention at a dosage ratio of about 0.30-0.75:1 (such as about 0.33-0.7:1).

Transplant patients being treating with cyclosporin instead of tacrolimus, can be converted to the extended release tacrolimus dosage form. The initial dose can be that discussed above (e.g., about 0.15 to about 0.20 mg/kg). Tacrolimus therapy can be initiated 12 to 24 hours after discontinuation of cyclosporin.

In one preferred embodiment, the once-daily extended release tacrolimus dosage form(s) described herein are administered once daily at the same time, consistently, with or without food. The extended release tacrolimus dosage form is preferably not taken with an alcoholic beverage or grapefruit juice and is not chewed, divided, or crushed.

Extended Release Oral Dosage Form

Dissolution and Pharmacokinetics

The oral dosage form releases the tacrolimus over an extended period of time, for example, over a period of at least 12, 13, 14, 15, 18, 20, 22, or 24 hours. For example, the release may be sufficiently slow that more than half of the tacrolimus in the dosage form is absorbed in the lower gastrointestinal tract. The release may be sufficiently slow to enable a very low absorption rate whereby its $C_{max}$ is lower than that for an immediate release formulation (such as Prograf) and the minimum concentration (before the next once daily dose is taken) is greater than that for a twice-daily immediate release formulation securing efficacy of the treatment for the full dosing interval of 24 hours.

The fluctuation, peak-trough fluctuation, and/or swing of tacrolimus (total and/or free) blood concentrations (from time 0 to 24 hours) resulting from a single dose of the extended release oral dosage form is significantly less than that for Prograf. In one embodiment, the fluctuation resulting from the extended release dosage form is less than 110, 100, 90, 80, 75, 70, 60, or 50%. In another embodiment, the swing resulting from the extended release dosage form is less than 120, 110, 100, 90, 80, 70, or 60%. In yet another embodiment, the peak-trough fluctuation is less than 400, 350, 300, 250, or 200%.

In another embodiment, the fluctuation and/or swing of tacrolimus (total and/or free) blood concentrations (from time 0 to 24 hours) resulting from the extended release dosage form when administered once daily in steady state (e.g., after 7 days of once daily administration) is significantly less than that for Prograf. In one embodiment, the fluctuation resulting from the extended release dosage form when administered once daily in steady state (e.g., after 7 days of once daily administration) is less than 100, 90, 80, 75, 70, 60, or 50%. In another embodiment, the swing resulting from the extended release dosage form when administered once daily in steady state (e.g., after 7 days of once daily administration) is less than 120, 110, 100, 90, 80, 70, or 60%.

In yet another embodiment, the fluctuation, peak-trough fluctuation, and/or swing of the blood concentrations, as measured after a single dose or in steady state (e.g., after 7 days of once daily administration) is less than that observed for Prograf® and/or Advagraf®. The decrease is preferably at least 10%, such as at least 20%, 30%, 40%, or 50%.

The dosage form upon oral administration may exhibit a $C_{max}$ that is significantly lower than that of an immediate release tacrolimus formulation such as Prograf®, either after a single dose or at steady state. In one embodiment, the extended release dosage form exhibits a $C_{max}$ that is at most about 80% of that for an immediate release tacrolimus formulation (e.g., Prograf®) (e.g., at most 75, 70, 65, 60, 55, or 50% of that of Prograf®) when measured after administration of a single dose. In another embodiment, the extended release dosage form exhibits a $C_{max}$ that is at most about 80% of that for an immediate release tacrolimus formulation (e.g., Prograf®) (e.g., at most 75, 70, 65, 60, 55, or 50% of that of Prograf®) when measured after administration at steady state. In yet another embodiment, the extended release dosage form exhibits a $C_{max}$ that is at most about 80% of that for Advagraf®, e.g., at most 75, 70, 65, 60, 55, or 50% of that of Advagraf® when measured after administration of a single dose. In yet another embodiment, the extended release dosage form exhibits a $C_{max}$ that is at most about 80% of that for Advagraf®, e.g., at most 75, 70, 65, 60, 55, or 50% of that of Advagraf® when measured after administration at steady state.

The dosage form, when administered at steady state, may provide a $t_{max}$ of from about 4 to 8 hours, such as about 5 to 7 hours or approximately 6 hours.

The dosage form upon oral administration may release the tacrolimus such that absorption of the tacrolimus takes place substantially in the colon (such as one or more locations of the colon ascendens, colon transversum and colon decendens) and/or the lower ileum. For example, in one embodiment, the dosage form releases at least 50, 60, 70, 80, or 90% of the tacrolimus in the lower gastrointestinal tract, such as the colon. In another embodiment, the dosage form releases at least 50, 60, 70, 80, or 90% of the tacrolimus in colon ascendens, colon transversum, colon decendens, or any combination of any of the foregoing.

The dissolution profile for the extended release oral dosage form is preferably measured by USP II dissolution test (paddle) method in 900 ml of an aqueous medium at pH 4.5 (adjusted with 2 N acetic acid) and comprising 0.005% hydroxypropylcellulose and 0.5% of the surfactant sodium lauryl sulfate (SLS), at 37° C.±0.5° C. and a paddle speed of 100 rpm.

Alternatively, the dissolution profile for the extended release oral dosage form can be measured by USP II dissolution test (paddle) or USP I dissolution test (basket) method in a medium at pH 4.5 and comprising 0.005% hydroxypropylcellulose, and a rotation of 50 rpm.

In yet another embodiment, the dissolution profile can be measured by Japanese Pharmacopoeia (13$^{th}$ Ed.), Dissolution Test, No. #2 (Paddle method, 50 rpm), using a test solution which is an aqueous 0.005% hydroxypropyl cellulose solution adjusted to pH 4.5. In one embodiment, the dosage form releases less than 63.2% of the tacrolimus in the dosage form at 15 hours as measured by Japanese Pharmacopoeia (13$^{th}$ Ed.), Dissolution Test, No. #2 (Paddle method, 50 rpm), using a test solution which is an aqueous 0.005% hydroxypropyl cellulose solution adjusted to pH 4.5.

In one embodiment, the dosage form releases at most 63.5% of the tacrolimus in the dosage form at the 12 hours time point, when tested according to USP II dissolution test (paddle) method in 900 ml of an aqueous medium at pH 4.5 and comprising 0.005% hydroxypropylcellulose and 0.5% of the surfactant sodium lauryl sulfate, at 37° C.±0.5° C. and a paddle speed of 100 rpm. In another embodiment, at most 63.5% of the tacrolimus is released at the 13 time hour point, 14 time hour point, or 15 time hour point. In yet another embodiment, the dosage form releases at least about 50% w/w of the total amount of tacrolimus within about 24 hours, such as, e.g., within about 22 hours, within about 20 hours, within about 18 hours, within about 15 hours or within about 12 hours. In yet another embodiment, 63.5% of the tacrolimus is released within 20 hours, such as 18 hours, 16 hours or 15.5 hours.

In yet another embodiment, (i) at most 63.5% of the tacrolimus is released at the 12 hour time point, and (ii) at least 8% of the tacrolimus is released at 4 hours and/or at least 15% of the tacrolimus is released at hour 8.

In another embodiment, the extended release oral dosage form provides a substantially zero order release for a majority of the release. In one embodiment, the oral dosage form provides a substantially zero order release of the tacrolimus in the colon and/or the lower ileum. For example, the dosage form may provide a substantially zero order release from 8 hours to 15 hours (for example, when tested according to USP II dissolution test (paddle) method in 900 ml of an aqueous medium at pH 4.5 and comprising 0.005% hydroxypropylcellulose and 0.5% of the surfactant sodium lauryl sulfate, at 37° C.±0.5° C. and a paddle speed of 100 rpm). In another embodiment, the dosage form provides a substantially zero order release from 2 hours to 10 hours (for example, when tested according to USP II dissolution test (paddle) method in 900 ml of an aqueous medium at pH 4.5 and comprising 0.005% hydroxypropylcellulose and 0.5% of the surfactant sodium lauryl sulfate, at 37° C.±0.5° C. and a paddle speed of 100 rpm).

In yet another embodiment, the addition of a surfactant to the release medium provides a release rate of the tacrolimus whereby the release of at most 80% of the tacrolimus is extended for a period of at least 7 hours, such as at least 8 hours, such as at least 9 hours, such as at least 10 hours, such as at least 11 hours, such as at least 12 hours such as at least 13 hours when tested in vitro according to USP II dissolution test (paddle) method in 900 ml of an aqueous medium at pH 4.5 and comprising 0.005% hydroxypropylcellulose and 0.5% of the surfactant sodium lauryl sulfate, at 37° C.±0.5° C. and a paddle speed of 100 rpm.

In one embodiment, 80% of the tacrolimus is released within 24 hours, such as 23 hours, 22 hours, 21 hours, 20 hours, 19 hours, 18 hours, 17 hours, or 16 hours, when tested in vitro according to USP II dissolution test (paddle) method in 900 ml of an aqueous medium at pH 4.5 and comprising 0.005% hydroxypropylcellulose and 0.5% of the surfactant sodium lauryl sulfate, at 37° C.±0.5° C. and a paddle speed of 100 rpm.

In one embodiment, release of the tacrolimus begins within 120 minutes such as within 90 minutes, such as within 60 minutes after deposition of the dosage form in the dissolution apparatus when tested in vitro according to USP II dissolution test (paddle) method in 900 ml of an aqueous medium at pH 4.5 and comprising 0.005% hydroxypropylcellulose and 0.5% of the surfactant sodium lauryl sulfate, at 37° C.±0.5° C. and a paddle speed of 100 rpm.

The dosage form may also have one or more of the following release characteristics:

a) The dosage form releases at most about 20% w/w of the tacrolimus within 1 hours, or within 2 hour, or within 3 hours, or within 4 hours or within 5 hours, when tested in vitro according to USP II dissolution test (paddle) method in 900 ml of an aqueous medium at pH 4.5 and comprising 0.005% hydroxypropylcellulose and 0.5% of the surfactant sodium lauryl sulfate, at 37° C.±0.5° C. and a paddle speed of 100 rpm, or another dissolution test method described herein.

b) The dosage form releases 40% w/w of the tacrolimus within 10 to 14 hours such as, e.g., within about 11 to 13 hours, when tested in vitro according to USP II dissolution test (paddle) method in 900 ml of an aqueous medium at pH 4.5 and comprising 0.005% hydroxypropylcellulose and 0.5% of the surfactant sodium lauryl sulfate, at 37° C.±0.5° C. and a paddle speed of 100 rpm, or another dissolution test method described herein.

c) The dosage form releases 20% w/w of the total amount of tacrolimus released within 6 to 10 hours such as, e.g., within about 7 to 9 hours, when tested in vitro according to USP II dissolution test (paddle) method in 900 ml of an aqueous medium at pH 4.5 and comprising 0.005% hydroxypropylcellulose and 0.5% of the surfactant sodium lauryl sulfate, at 37° C.±0.5° C. and a paddle speed of 100 rpm, or another dissolution test method described herein.

d) The dosage form releases 50% w/w of the tacrolimus within 13 to 17 hours such as, e.g., within about 14 to 16 hours, when tested in vitro according to USP II dissolution test (paddle) method in 900 ml of an aqueous medium at pH 4.5 and comprising 0.005% hydroxypropylcellulose and 0.5% of the surfactant sodium lauryl sulfate, at 37° C.±0.5° C. and a paddle speed of 100 rpm, or another dissolution test method described herein.

e) The dosage form provides a release profile which is substantially linear in the period from 4 to 8 hours defined as a gradient or slope being within 25% of the gradient or slope measured at hour 6, such as within 15%, preferable within 10%.

f) The dosage form provides a release profile which is substantially linear in the period from 6 to 10 hours defined as a gradient or slope being within 25% of the gradient or slope measured at hour 8, such as within 15%, preferable within 10%.

g) The dosage form provides a release profile which is substantially linear in the period from 8 to 12 hours defined as a gradient or slope being within 25% of the gradient or slope measured at hour 10, such as within 15%, preferable within 10%.

h) The dosage form provides a release profile which is substantially linear in the release period from the time point where 20% is released to the time point where 50 or 80% is released defined as a gradient or slope at the 50 or 80% time point being within 25% of the gradient or slope measured at the 20% time point.

i) The release extending mechanism of the dosage form is not a permeation controlling coat.

In other embodiments, the following conditions are fulfilled with respect to in vitro dissolution tests performed by USP II dissolution test (paddle) method in 900 ml of an aqueous medium at pH 4.5 and comprising 0.005% hydroxypropylcellulose and 0.5% of the surfactant sodium lauryl sulfate, at 37° C.±0.5° C. and a paddle speed of 100 rpm.

i) at most about 30% w/w such as, e.g., at most about 25% w/w, at most about 20% w/w, at most about 15% w/w or at most about 10% w/w of the tacrolimus is released within 2 hours;

ii) at most about 10% w/w such as, e.g., at most about 7.5% w/w, at most about 5% w/w or at most about 2.5% w/w of tacrolimus is released within 2 hours;

iii) at most about 60% w/w such as, e.g., at most about 50% w/w, at most about 40% w/w or at most about 30% w/w of tacrolimus is released within 15 hours such as, e.g., within about 12 hours;

iv) at most about 40% w/w such as, e.g., at most about 30% w/w, at most about 25% w/w or at most about 20% w/w of tacrolimus is released within 6 hours; and/or v) at most about 30% w/w such as, e.g., at most about 25% w/w, at most about 20% w/w or at most about 15% w/w of tacrolimus is released within 4 hours.

The dosage form of the present invention may provide greater bioavailability than Prograf. In one embodiment, the $AUC_{Dosage\ Form}/AUC_{Prograf®}$ value is at least about 1.25 such as about 1.5 or more, about 1.8 or more, about 1.9 or more, about 2.0 or more.

The dosage form according to the invention may provide and reduce or abolish the need for administration in connection with food intake, which provide for a higher degree of freedom for the recipient of the dosage forms, and consequently the patients acceptance and/or compliance may be significantly improved. Furthermore, the dosage forms may provide a significant reduction in side effects, especially side effect related to a high peak concentration (such as, e.g., nephro- and neuro-toxicity (including tremors), diarrhea, constipation, abdominal pain, and nausea).

The dosage form may have a $C_{diff}=[C_{max}-C_t(t=12\ hours)]$ that is less than that of Prograf® under the same conditions. If $C_{diff}$ for Prograf® is set to 100 then $C_{diff}$ of a dosage form according to the invention may be 90 or less such as, e.g., about 85 or less, about 80 or less, about 75 or less, about 70 or less, about 65 or less, about 60 or less, about 55 or less, about 50 or less, about 45 or less or about 40 or less.

The dosage form may release tacrolimus in a pH dependent or pH independent manner.

Upon oral administration to a subject, the dosage form may release tacrolimus in such a manner that a plasma concentration of at least about 5 ng/ml such as, e.g., at least about 7.5 ng/mL or at least about 10 ng/mL for a time period of at least about 24 hours is obtained. In one embodiment, the difference between the peak plasma concentration and plasma concentration measured 24 hours after administration is at most about 20 ng/mL such as, e.g., at most about 10 ng/ml, at most about 7.5 ng/mL or at most about 5 ng/mL. Preferably, the extended release dosage form(s) when administered maintain the subject's whole blood pre-dose (trough) tacrolimus concentration between about 5 and 20 ng/ml, such as from about 7 to about 20 ng/ml, from about 5 to about 15 ng/ml, or from about 6 to about 14 ng/ml.

In one embodiment, the extended release dosage form exhibits little to no diurnal effect. In a preferred embedment the difference in bioavailability is substantially independent of the time of the day the dosage is administered. This provides the possibility of a once daily dosage regimen at bedtime or in the evening in addition to the normal morning dosing. For example, according to one embodiment, the extended release dosage form when administered to a subject after at least 4 hours fasted state in the evening provides a bioavailability which, relative to that obtained after administration of the dosage form in the morning after at least 4 hours fasted state, is at least 70, 80, 85, 90, or 95% of the value measured after administration in the morning. In another embodiment, the dosage form when administered to a subject after at least 4 hours fasted state in the evening provides a $C_{max}$, which relative to that obtained after administration of the dosage form in the morning after at least 4 hours fasted state, is at least 70, 80, 85, 90, or 95% of the value measured after administration in the morning.

Formulation

The extended release oral dosage forms may include a dispersion or solution of the tacrolimus (e.g., a solid dispersion or solid solution). The tacrolimus may be dispersed or dissolved in a hydrophilic or water-miscible vehicle. The vehicle preferably has a melting point (or pour point) of at least 20° C. The physical state of the dispersion and/or solution may be determined by using various techniques such as Hot Stage Microscopy (HSM), Differential Scanning Calorimetry (DSC), Scanning Electron Microscopy (SEM) optionally in combination with Energy Dispersive X-ray (EDX), and X-ray powder diffraction. In one embodiment, the tacrolimus is fully dissolved in the vehicle to form a solid solution at ambient temperature.

In one embodiment, the concentration of tacrolimus in the vehicle is between about 0.01% w/w and about 15% w/w, such as from about 0.1 to about 10% w/w, from about 0.5 to about 5% w/w, or from about 1 to about 4% w/w (based upon 100% total weight of the dosage form). For example, the concentration of tacrolimus can be at most 10, 8, 5, 4, 3, or 2% w/w. The concentration of tacrolimus in the vehicle can be at least 0.05, 0.1, 0.5, 0.7, or 1% w/w.

The hydrophilic or water-miscible vehicle to be used according to the invention is preferably one having a melting point (freezing point or pour point) of at least 20° C., such as at least 30, 40, 50, 52, 55, 59, 61 or 65° C.

Examples of useful hydrophilic or water-miscible vehicles to be used according to this invention are selected from the group consisting of polyethylene glycols, polyoxyethylene oxides, poloxamers, polyoxyethylene stearates, poly-epsilon caprolactone, polyglycolized glycerides (such as (i) mixtures of monoesters, diesters and/or triesters of glycerides of long chain ($C_{12}$ to $C_{18}$) fatty acids, (ii) PEG (mono- and/or di) esters of long chain ($C_{12}$ to $C_{18}$) fatty acids, and (iii) Gelucire® excipients, e.g. Gelucire® 50/13), and mixtures thereof. Other useful hydrophilic or water-miscible vehicles include, but are not limited to, polyvinylpyrrolidones, polyvinyl-polyvinylacetate copolymers (PVP-PVA), polyvinyl alcohol (PVA), polymethacrylic polymers (Eudragit RS; Eudragit RL, Eudragit NE, Eudragit E), cellulose derivatives (including hydroxypropyl methylcellulose (HPMC), hydroxypropyl cellulose (HPC), methylcellulose, sodium carboxymethylcellulose, and hydroxyethyl cellulose), pectins, cyclodextrins, galactomannans, alginates, carragenates, xanthan gums and mixtures thereof.

Further examples of substances useful as vehicles are:

i) polyethoxylated fatty acids such as, e.g. fatty acid mono- or diesters of polyethylene glycol or mixtures thereof such as, e.g. mono- or diesters of polyethylene glycol with lauric acid, oleic acid, stearic acid, myristic acid, and ricinoleic acid, and the polyethylene glycol may be selected from PEG 4, PEG 5, PEG 6, PEG 7, PEG 8, PEG 9, PEG 10, PEG 12, PEG 15, PEG 20, PEG 25, PEG 30, PEG 32, PEG 40, PEG 45, PEG 50, PEG 55, PEG 100, PEG 200, PEG 400, PEG 600, PEG 800, PEG 1000, PEG 2000, PEG 3000, PEG 4000, PEG 5000, PEG 6000, PEG 7000, PEG 8000, PEG 9000, PEG 1000, PEG 10,000, PEG 15,000, PEG 20,000, and PEG 35,000;

ii) polyethylene glycol glycerol fatty acid esters, i.e. esters such as the above-mentioned but in the form of glyceryl esters of the individual fatty acids;

iii) glycerol, propylene glycol, ethylene glycol, PEG or sorbitol esters with e.g. vegetable oils such as hydrogenated castor oil, almond oil, palm kernel oil, castor oil, apricot kernel oil, olive oil, peanut oil, or hydrogenated palm kernel;

iv) polyglycerized fatty acids such as polyglycerol stearate, polyglycerol oleate, polyglycerol ricinoleate, and polyglycerol linoleate;

v) propylene glycol fatty acid esters such as propylene glycol monolaurate and propylene glycol ricinoleate;

vi) mono- and diglycerides such as glyceryl monooleate, glyceryl dioleae, glyceryl mono- and/or dioleate, glyceryl caprylate, and glyceryl caprate;

vii) sterol and sterol derivatives;

viii) polyethylene glycol sorbitan fatty acid esters (PEG-sorbitan fatty acid esters) such as esters of PEG with the various molecular weights indicated above, and the various Tween® series;

ix) polyethylene glycol alkyl ethers such as PEG oleyl ether and PEG lauryl ether;

x) sugar esters such as sucrose monopalmitate and sucrose monolaurate;

xi) polyethylene glycol alkyl phenols such as the Triton® X or N series;

xii) sorbitan fatty acid esters such as the Span® series or Ariacel® series, e.g. sorbinan monolaurate, sorbitan monopalmitate, sorbitan monooleate, and sorbitan monostearate;

xiii) lower alcohol fatty acid esters such as oleate, isopropyl myristate, and isopropyl palmitate; and xiv) ionic surfactants including cationic, anionic and zwitterionic surfactants such as fatty acid salts, bile salts, phospholipids, phosphoric acid esters, carboxylates, sulfates and sulfonates.

In one preferred embodiment, the vehicle is a polyethylene glycol (PEG), in particular a PEG having an average molecular weight of at least 1500, preferably at least 3000, more preferably at least 4000, such as at least 6000. For example, the PEG may have an average molecular weight ranging from 1500 to 35000, from 3000 to 35000, from 3000 to 20000, from 4000 to 20000, from 3000 to 10000, or from 4000 to 10000. The PEG can be, for example, PEG 3000, PEG 4000, PEG 6000, or PEG 8000. The polyethylene glycol may advantageously be mixed with one or more other hydrophilic or water-miscible vehicles, for example a poloxamer, preferably in a proportion (on a weight/weight basis) of between 1:3 and 10:1, such as between 1:1 and 5:1, between 3:2 and 4:1, between 2:1 and 3:1, or about 7:3. A specific example of a useful mixture is a mixture of PEG6000 and poloxamer 188 in the ratio of 7:3.

Suitable poloxamers (also known as polyoxypropylene-polyoxyethylene block copolymers) include, but are not limited to, poloxamer 188, poloxamer 237, poloxamer 338, poloxamer 407, and other block copolymers of ethylene oxide and propylene oxide such as the Pluronic® and/or Tetronic© series. Suitable block copolymers of the Pluronic® series include polymers having a molecular weight of about 3,000 or more such as, e.g. from about 4,000 to about 20,000 and/or a viscosity (Brookfield) from about 200 to about 4,000 cps such as, e.g., from about 250 to about 3,000 cps. Suitable examples include Pluronic® F38, P65, P68LF, F75, F77, P84, P85, F87, F88, F98, P103, P104, P105, F108, P123, F123, F127, 10R8, 17R8, 25R5, and 25R8. Suitable block copolymers of the Tetronic® series include polymers having a molecular weight of about 8,000 or more such as, e.g., from about 9,000 to about 35,000 and/or a viscosity (Brookfield) of from about 500 to about 45,000 cps such as, e.g., from about 600 to about 40,000. The viscosities given above are determined at 60° C. for substances that are pastes at room temperature and at 77° C. for substances that are solids at room temperature. In a preferred embodiment of the present invention, the poloxamer is poloxamer 188, which has an average molecular weight of about 8400 and a melting point of about 50-54° C.

The extended release oral dosage form may be that described in WO 05/020993, US 2006/0287352, US 2010/0105717 or US 2011/0201639, each of which is hereby incorporated by reference in its entirety. In one embodiment, the extended release oral dosage form is that described in Example 20 of US 2010/0105717.

In another embodiment, the tacrolimus is dissolved or dispersed in a hydrophobic vehicle, such as an oil, an oily material, sorption material, a wax or a fatty acid derivative, e.g., a wax having a low melting point (for example glyceryl monostearate). For instance, the dosage form may include a sorption material selected from silica acid or a derivative or salt thereof including silicates, silicon dioxide (Aeroperl® 300 (available from Degussa, Frankfurt, Germany)) and polymers thereof, magnesium aluminosilicate and/or magnesium aluminometasilicate, bentonite, kaolin, magnesium trisilicate, montmorillonite, saponite, and any combination of any of the foregoing. These sorption materials are useful for containing oils or oily-like materials.

The dosage form may include other excipients, such as modifying release agents, fillers, diluents, disintegrants, binders, glidants, lubricants, and any combination of any of the foregoing. Other pharmaceutically acceptable excipients which may be included in the dosage form include, but are not limited to, acidifying agents, alkalizing agents, preservatives, stabilizing agents, antioxidants, pH-adjusting agents, buffering agents, chelating agents, coloring agents, complexing agents, emulsifying and/or solubilizing agents, surface-active agents, absorption enhancing agents, flavors and perfumes, taste-masking agents, wetting agents, humectants, sweetening agents, wetting agents, and any combination of any of the foregoing.

Examples of release modifying agents include, but are not limited to, hydrophilic polymers such as hydroxypropyl cellulose (HPC), hydroxypropyl methyl cellulose (HPMC), methyl cellulose, poly (N-vinyl-2-pyrrolidinone) (PVP), poly(ethylene oxide) (PEO), poly(vinyl alcohol) (PVA), xanthan gum, carrageenan, and other such natural and synthetic materials. A preferred release modifying agent is HPMC.

Examples of suitable fillers, diluents and/or binders include lactose (e.g. spray-dried lactose, α-lactose, β-lactose, Tabletose®, various grades of Pharmatose®, Microtose® or Fast-Floc®), microcrystalline cellulose (various grades of Avicel®, Elcema®, Vivacel®, Ming Tai® or Solka-Floc®), hydroxypropylcellulose, L-hydroxypropylcellulose (low substituted), hydroxypropyl methylcellulose (HPMC) (e.g. Methocel E, F and K, Metolose SH of Shin-Etsu, Ltd, such as, e.g. the 4,000 cps grades of Methocel E and Metolose 60 SH, the 4,000 cps grades of Methocel F and Metolose 65 SH, the 4,000, 15,000 and 100,000 cps grades of Methocel K; and the 4,000, 15,000, 39,000 and 100,000 grades of Metolose 90 SH), methylcellulose polymers (such as, e.g., Methocel A, Methocel A4C, Methocel A15C, Methocel A4M), hydroxyethylcellulose, sodium carboxymethylcellulose, carboxymethylene, carboxymethylhydroxyethylcellulose and other cellulose derivatives, sucrose, agarose, sorbitol, mannitol, dextrins, maltodextrins, starches or modified starches (including potato starch, maize starch and rice starch), calcium phosphate (e.g. basic calcium phosphate, calcium hydrogen phosphate, dicalcium phosphate hydrate), calcium sulfate, calcium carbonate, sodium alginate, and collagen.

Examples of diluents include calcium carbonate, dibasic calcium phosphate, tribasic calcium phosphate, calcium sulfate, microcrystalline cellulose, powdered cellulose, dextrans, dextrin, dextrose, fructose, kaolin, lactose, mannitol, sorbitol, starch, pregelatinized starch, sucrose, and sugar.

Examples of disintegrants include alginic acid or alginates, microcrystalline cellulose, hydroxypropyl cellulose and other cellulose derivatives, croscarmellose sodium, crospovidone, polacrillin potassium, sodium starch glycolate, starch, pregelatinized starch, and carboxymethyl starch (e.g. Primogel® and Explotab®).

Examples of binders include acacia, alginic acid, agar, calcium carrageenan, sodium carboxymethylcellulose, microcrystalline cellulose, dextrin, ethylcellulose, gelatin, liquid glucose, guar gum, hydroxypropyl methylcellulose, methylcellulose, pectin, PEG, povidone, and pregelatinized starch.

Examples of glidants and lubricants include stearic acid, magnesium stearate, calcium stearate or other metallic stearate, talc, waxes and glycerides, light mineral oil, PEG, glyceryl behenate, colloidal silica, hydrogenated vegetable oils, corn starch, sodium stearyl fumarate, polyethylene glycols, alkyl sulfates, sodium benzoate, and sodium acetate.

Examples of antioxidants include ascorbic acid, ascorbyl palmitate, butylated hydroxyanisole, butylated hydroxytoluene, hypophosphorous acid, monothioglycerol, potassium metabisulfite, propyl gallate, sodium formaldehyde sulfoxylate, sodium metabisulfite, sodium thiosulfate, sulfur dioxide, tocopherol, tocopherol acetate, tocopherol hemisuccinate, and TPGS and other tocopherol derivatives.

The dosage form may, for example, contain an antioxidant and/or a stabilizing agent at a concentration ranging from about 0.1% w/w to about 5% w/w.

When a surfactant or a mixture of surfactants is present in the dosage form, the concentration of the surfactant(s) may range from about 0.1-80% w/w, such as from about 0.1 to about 20% w/w, from about 0.1 to about 15% w/w, from about 0.5 to about 10% w/w, from about 10 to about 70% w/w, from about 20 to about 60% w/w or from about 30 to about 50% w/w.

The stabilizing agent may be a pH-regulating pharmaceutical excipient. Preferably, the stabilizing agent is capable of providing a pH below 7 in the dosage form, as measured after re-dispersing the dosage form in water, for example, a pH in the range of 2.5 to 5 or 2.5 to 4 or 3 to 3.6 or 3 to 3.5. Suitable stabilizing agents include, but are not limited to, inorganic acids, inorganic bases, inorganic salts, organic acids, organic bases, and pharmaceutically acceptable salts thereof. The stabilizing agent can be a chelating agent. For instance, the stabilizing compound can be an organic acid selected from mono-, di-, oligo and polycarboxylic acids, for example succinic acid, citric acid, tartaric acid, acrylic acid, benzoic acid, malic acid, maleic acid, oxalic acid, sorbic acid and mixtures thereof. In one preferred embodiment, the stabilizing agent is oxalic acid, tartaric acid and/or citric acid. One preferred stabilizing agent is tartaric acid.

The dosage form may include a stabilizing effective amount of stabilizing agent (for instance, an amount effective to prevent or decrease the rate of formation of tacrolimus degradation products). In one embodiment, the amount of stabilizing agent ranges from about 0.05% w/w to about 5% w/w, based upon the total weight of tacrolimus, vehicle and stabilizing agent. The dosage form may contain at least 0.05% w/w, at least 0.1% w/w, or at least 0.2% w/w and less than 3% w/w, less than 2% w/w, less than 1% w/w, less than 0.8% w/w, or not more than 0.6% w/w of the stabilizing agent.

Apart from tacrolimus, the dosage form may also comprise a further therapeutically, prophylactically and/or diagnostically active substance, such as steroids, calcineurin inhibitors and/or anti-proliferative agents. Examples of active substances which can be included in the dosage form include prednisone, prednisolone, methylprednisone, cyclosporin, mycophenolate mofetil, azathioprine, sirolimus, everolimus, mycophenolate sodium, and FTY720 (Novartis).

In one embodiment, at least a part of the tacrolimus is present in the form of a solid solution or a solid dispersion. For example, 10% or more such as 20, 30, 40, 50, 60, 70, 80, 90, 95% or more, or about 100% w/w of the tacrolimus is present in the dosage form in the form of a solid solution or a solid dispersion.

A solid dispersion may be obtained, for example, by employing organic solvents or by dispersing or dissolving the tacrolimus in another suitable medium (e.g. an oil or an oily-like material that is in liquid form at room temperature or at elevated temperatures). Solid dispersions (solvent method) may for example be prepared by dissolving a physical mixture of the tacrolimus and the vehicle (e.g., a hydrophilic polymer) in a common organic solvent, followed by evaporation of the solvent. Suitable organic solvents include, but are not limited to, solvents in which the tacrolimus is soluble such as methanol, ethanol, methylene chloride, chloroform, ethylacetate, acetone or mixtures thereof. The solid dispersion may also be formed by spray drying techniques, controlled agglomeration, freeze-drying or coating on carrier particles or any other solvent removal process. For instance, the tacrolimus may be dispersed and/or dissolved in a vehicle by a controlled agglomeration method. Stabilizing agents may be added in order to ensure the stability of the solid dispersion or solution.

A preferred method is described in International Publication No. WO 03/004001, which is hereby incorporated by reference. The method comprises spraying a first composition in liquid form, where the first composition comprises a first vehicle or carrier and having a melting point above 5° C. onto a second composition comprising a second support or carrier material, the second composition e.g. being in the fluidized state and having a temperature below the melting point of the first vehicle or carrier. The tacrolimus may be present in the first vehicle or carrier composition and/or in the second support or carrier composition. In one embodiment, the tacrolimus is dissolved in the first composition. The melting point of the carrier or vehicle may be in the range of 10° C. to 150° C., such as 30° C. to 100° C. or 40° C. to 50° C.

The controlled agglomeration method can produce particles of a desirable particle size. In one embodiment, the particulate material formed by controlled agglomeration has a geometric weight mean diameter $d_{gw}$ of $\geq 10$ µm, such as $\geq 20$ µm, from about 20 to about 2000 µm, from about 30 to about 2000 µm, from about 50 to about 2000 µm, from about 60 to about 2000 µm, from about 75 to about 2000 µm, from about 100 to about 1500 µm, from about 100 to about 1000 µm, from about 100 to about 700 µm, at most about 400 µm, at most 300 µm, from about 50 to about 400 µm, from about 50 to about 350 µm, from about 50 to about 300 µm, from about 50 to about 250 µm or from about 100 to about 300 µm.

Polymers containing acidic functional groups may be suitable for solid dispersions, which release the tacrolimus in a preferred pH range providing acceptable absorption in the intestines. Such polymers may be one ore more selected from the group comprising hydroxypropyl methylcellulose phtalate (HMPCP), polyvinyl acetate phtalate (PVAP), hydroxypropylmethylcellulose acetate succinate (HPMCAS), alginate, carbomer, carboxymethylcellulose, methacrylic acid copolymer (Eudragit L, Eudragit S), shellac, cellulose acetate phthalate (CAP), starch glycolate, polacrylin, methyl cellulose acetate phtalate, hydroxypropyulcellulose acetate phthalate, cellulose acetate terephtahalate, cellulose acetate isophthalate and cellulose acetate trimellitate.

The weight ratio of tacrolimus to polymer in the solid dispersion may range from about 3:1 to about 1:20, such as from about 3:1 to about 1:5, or from about 1:1 to about 1:3.

The desired release profile of the dosage form may be provided by using one or more of the following formulation techniques:
  i) coating the dosage form with an enteric coating; and/or
  ii) incorporating one or more modifying release agents in the dosage form (for example, with the tacrolimus and vehicle).

The modifying release agent can be, for example, included in the extra-granular phase. For example, a solid dispersion or solid solution of tacrolimus can be prepared as discussed above (e.g., by controlled agglomeration) and the resulting particles can be mixed with an extragranular phase containing a release-modifying agent.

An entero-coated formulation may have the disadvantage of delaying the release without extending the release and preferably therefore is used in combination with an extending technology. This type of coating is resistant to release of the tacrolimus until a certain pH is reached. The film alters properties and becomes permeable at a certain pH. Examples of pH-sensitive polymers, which are relatively insoluble and impermeable at the pH of the stomach, but which are more soluble and permeable at the pH of the small intestine and colon include, but are not limited to polyacrylamides, phthalate derivatives such as acid phthalates of carbohydrates, amylose acetate phthalate, cellulose acetate phthalate, other cellulose ester phthalates, cellulose ether phthalates, hydroxypropylcellulose phthalate, hydroxypropylethylcellulose phthalate, hydroxypropylmethylcellulose phthalate, methylcellulose phthalate, polyvinyl acetate phthalate, polyvinyl acetate hydrogen phthalate, sodium cellulose acetate phthalate, starch acid phthalate, styrene-maleic acid dibutyl phthalate copolymer, styrene-maleic acid polyvinylacetate phthalate copolymer, styrene and maleic acid copolymers, polyacrylic acid derivatives such as acrylic acid and acrylic ester copolymers, polymethacrylic acid and esters thereof, poly acrylic methacrylic acid copolymers, shellac, and vinyl acetate and crotonic acid copolymers. pH-sensitive polymers of specific interest include shellac; phthalate derivatives, particularly cellulose acetate phthalate, polyvinylacetate phthalate, and hydroxypropylmethylcellulose phthalate; polyacrylic acid derivatives, particularly polymethyl methacrylate blended with acrylic acid and acrylic ester copolymers; and vinyl acetate and crotonic acid copolymers.

The release may also be pH independent, e.g., by providing the dosage form with a controlled release coating such as, e.g. a cellulose based coating (for example, ethylcellulose) or by providing the composition in the form of a matrix composition such as, e.g., a hydrophilic cellulose polymer matrix type e.g. based on HPMC. A combination may also be employed.

In one embodiment, the dosage form comprises (a) granules of tacrolimus and a hydrophilic vehicle (such as PEG, poloxamer, or a mixture thereof) in the pores of and/or on an inert porous solid carrier (such as lactose, e.g., lactose monohydrate), and (b) one or more release modifying agent(s) (e.g., HPMC). For instance, a tablet can be prepared by compressing a mixture of these granules and release modifying agent(s). The granules can be prepared, for example, by spraying a mixture of tacrolimus in a melted hydrophilic vehicle onto the inert solid carrier. The tacrolimus is preferably dissolved in the melted vehicle. In one embodiment, the carrier has a $d_{50}$ less than 200, 100, 80, 75, or 50 microns. In another embodiment, the granules have a $d_{50}$ less than 1000, 800, 600, 400, 300, or 250 microns.

In another embodiment, the dosage form is a tablet comprising, by weight, about 30% to about 80% solid dispersion containing tacrolimus, about 15% to about 35% matrix former (such as HPMC), 0% to about 35% lactose, 0% to about 20% microcrystalline cellulose, and about 0.25% to about 2% lubricant (such as magnesium stearate).

The dosage form preferably contains less than 0.5% w/w of 8-epitacrolimus, a degradation product of tacrolimus upon storage (based upon 100% w/w of total tacrolimus and its degradation products). Also, the dosage form may be substantially free (e.g. contain less than 1, 0.5, 0.2, 0.1 or 0.05% w/w) of an organic solvent or organic solvent residues (based upon 100% w/w of the dosage form). In one embodiment, the dosage form comprises less than 0.1, 0.2, or 0.5% of 8-epitacrolimus after 1, 2, 4, 8, or 12 weeks or 3 or 6 months of storage at 25° C. at 60% relative humidity.

The dosage form may be in the form of, for example, tablets, capsules and sachets.

Suitable dosage forms (strength) range from 0.1 mg to 15 mg of tacrolimus. Preferred strengths for the dosage forms include 0.75, 1, and 4 mg. Other strengths for the dosage form include, but are not limited to, 2 and 5 mg.

Tacrolimus

The tacrolimus can be in any physical form (amorphous, crystalline form, such as a hydrate or anhydrate, or complex). In one preferred embodiment, the tacrolimus is in amorphous form. In another embodiment, the tacrolimus is tacrolimus monohydrate (shown below). The preparation of tacrolimus is described in, for example, EP-A-0 184 162. The tacrolimus can have a particle size ($d_{50}$) in microns or nanometers.

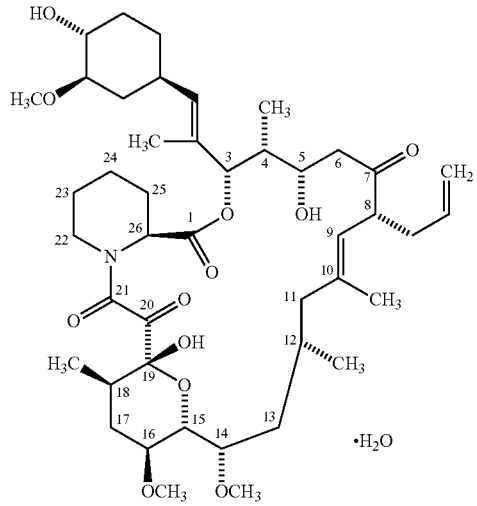

Tacrolimus (USP tricosine numbering)

The following examples serve the purpose of illustrating the invention and are not intended to limiting the scope of the present invention.

Example 1

Tacrolimus Extended Release Dosage Form

The 2 mg tacrolimus tablet (referred to as LCP-Tacro) provided below can be prepared as described in Example 20 of US 2010/0105717, which is herein incorporated by reference.

| Extended release composition, stabilized | LCP-Tacro 2 mg |
|---|---|
| Tacrolimus monohydrate (2.00 mg calculated on the anhydrous basis) | 2.0400 mg |
| Excipients | |
| Butylated hydroxytoluene | 10.200 µg |
| Dimethicone 350 | 0.25500 µg |
| Hypromellose 2208 (15,000 cp) | 62.866 mg |
| Lactose monohydrate | 41.727 mg |
| Magnesium stearate | 1.5716 mg |
| Opadry II white 85G18490 | 4.7232 mg |
| Poloxamer 188 | 14.688 mg |
| Polyethylene glycol 6,000 | 34.272 mg |
| Tartaric acid | 255.00 µg |

Similar 0.75, 1, and 4 mg tacrolimus containing tablets may be prepared.

Example 2

A clinical study was performed to evaluate the efficacy and safety of LCP Tacro (tacrolimus) tablets administered once daily compared to Prograf capsules twice daily as immunosuppression for the prevention of acute allograft rejection in de novo adult kidney transplant recipients treated for a 12 month study period followed by a 12 month, blinded extension treatment period.

This was a two-armed parallel group, prospective, randomized, double-blind, double-dummy, multicenter clinical study to establish the efficacy and safety of LCP-Tacro tablets once daily for the prevention of allograft rejection in de novo adult male and female recipients of a primary or secondary kidney transplant evaluated by a combined efficacy endpoint comprised of acute rejection, graft loss and patient loss. Recipients of a kidney transplant were randomly assigned to once-daily therapy with LCP-Tacro tablets or to twice-daily therapy with Prograf capsules, each concomitantly administered with mycophenolate mofetil (MMF) and corticosteroids. All patients also received an interleukin-2 (IL-2) receptor antagonist (e.g., Simulect®, basiliximab; Novartis Pharmaceuticals, East Hanover, NJ). Following screening, transplantation, and randomization, study visits were conducted over a 12-month treatment period, with additional visits during a 12 month extension period on treatment and a follow-up safety assessment by visit or telephone interview 30 days after withdrawal from study drug.

The de novo patients (18-70 years old) received a primary or secondary kidney transplant from a non-human leukocyte antigen (HLA) identical live donor or a deceased donor.

LCP-Tacro Dosage: The initial dose of 0.17 mg/kg was administered orally in the morning (before noon) within 48 hours following transplantation. Subsequent doses were adjusted according to whole blood tacrolimus trough levels. LCP-Tacro tablets were provided in 0.75, 1, and 4 mg dosage strengths.

Prograf Dosage: Starting total daily dose of 0.10 mg/kg was administered in two equally divided doses, one in the morning (before noon) and one in the evening, per product labeling. The first dose was administered in the morning (before noon) within 48 hours following transplantation. Subsequent doses were adjusted according to whole blood tacrolimus trough levels. Prograf capsules were provided in 0.5, 1, and 5 mg dosage strengths.

In the initial post-transplant period, whole blood trough levels were measured at 24 and 48 hours following the initial dose. The first dose adjustment based on measurement of whole blood tacrolimus levels generally took place 48 hours after the initial dose for both study drugs. However, if clinically indicated, the dose was adjusted at 24 hours post initial dose. Study drugs were adjusted to maintain the whole blood pre-dose (trough) concentration of tacrolimus in the target range of 6-11 ng/mL for the first 30 days, then 4-11 ng/mL for the remainder of the study.

Tacrolimus trough levels were measured at each study visit beginning 24 hours after the first dose of study medication. Tacrolimus whole blood trough levels were drawn within 30 minutes before the morning dosing.

Placebo: Matching placebos for both the test formulation and reference formulation were used in the study.

Concomitant Therapy:

(1) Antibody induction therapy: An IL-2 receptor antagonist (e.g., basiliximab) was administered according to currently approved product labeling (2 doses of 20 mg each, the first 20 mg dose was given within 2 hours prior to transplantation surgery. The recommended second 20 mg dose was given 4 days after transplantation).

Mycophenolate mofetil (MMF) was administered as per the most current product label (1 g administered twice daily (2 g daily dose)).

(2) Corticosteroids: Corticosteroids were required, but the regimen was based on the standard of care at the participating site. However, all patients were maintained for the first month on a minimum of 10 mg and, thereafter, on a minimum of 5 mg of prednisone or equivalent for the 360-day duration of the study. During the 12 month treatment extension period, the corticosteroid treatment was based on the standard of care at the participating site.

The use of polyclonal or monoclonal T-cell depleting antibodies, including but not limited to Thymoglobulin® (rabbit antithymocyte globulin) or Campath© (alemtuzumab) for induction, was not permitted. The use of Rapamune® (rapamycin, sirolimus), Certican® (everolimus) or investigational agents was not permitted.

The primary efficacy endpoint for the study was the proportion of treatment failures within 12 months after randomization to LCP-Tacro. A patient was considered a treatment failure if the patient experienced any of the following events during this period: death, graft failure, biopsy-proven acute rejection (BPAR) (Banff grade≥1A) or lost to follow-up.

Clinical decisions were based on local biopsy readings. All biopsies were also read by a central blinded reader and the central reading was considered the definitive data for purposes of the study. The diagnosis and severity assessment of acute rejection was made according to the Banff 2007 criteria.

Various efficacy and safety endpoints produced at 12-month time point were summarized for Months 18 and 24 by treatment groups.

After a screening visit and renal transplantation, there were 17 scheduled study visits (including randomization visit) during the 12 month treatment period and 4 scheduled visits during the extension period, and a follow-up safety telephone interview at Month 25 which was 30 days after the end of study drug treatment. Evaluations included measurement of vital signs, complete physical examinations, ECGs, assessments of AEs and concomitant drug use, laboratory tests (hematology, biochemistry [including hepatic, renal and lipid profiles], HbA1c, CMV and BKV and urinalysis), anti-HLA antibodies and determination of tacrolimus whole blood trough levels.

Results

The treatment failure results for LCP-Tacro and Prograf are provided below. From Month 3 on, the dose of LCP-Tacro was roughly 15% lower than the dose of Prograf required to achieve the same therapeutic blood levels.

| Treatment Failure | LCP-Tacro (N = 268) | Prograf (N = 275) |
| --- | --- | --- |
| Treatment failure within 12 months for all subjects | 49 (18.3%) | 54 (19.6%) |
| All-cause mortality | 8 (3.0%) | 8 (2.9%) |
| Graft failure | 9 (3.4%) | 11 (4.0%) |
| BPAR | 35 (13.1%) | 37 (13.5%) |
| Lost to follow-up | 4 (1.5%) | 5 (1.8%) |
| Treatment failure within 12 months for Black subjects | 3 (30.0%) | 6 (40.0%) |

The superior efficacy (lower treatment failure rate) of LCP-Tacro is consistent with a trend found in two prior clinical studies of one-year (or more). In one prior study (n=63), the LCP-Tacro group had a treatment failure rate of 6.3% while that of the Prograf group was 9.7%. In the other prior study (n=326), the LCP-Tacro group had a treatment failure rate of 2.5% versus 4.9% for Prograf.

LCP-Tacro also exhibited superior efficacy during the early post-transplant period. According to a Kaplan-Meier analysis of the time to occurrence of first biopsy-proven acute rejection (BPAR) during the first three months post-transplant, LCP-Tacro was superior to Prograf. Within the first 3 months after transplant, when patients are at the greatest risk of rejection, the treatment failure rates for LCP-Tacro and Prograf were 10.4% and 14.2%, respectively (p=0.124). Within the first 6 months after transplant, the treatment failure rates for LCP-Tacro and Prograf were 14.2% and 15.3%, respectively. This in contrast to Advagraf which was found in a prior clinical study to exhibit a quantitatively (though not statistically significant) worse time to occurrence of first BPAR by a similar analysis. Silva et al., *Am. J. Transplant*, 2007, 7:595-608 (see FIG. 3). LCP-Tacro also produced fewer clinically suspected and treated rejections than Prograf (13.8% vs. 15.6%). Additionally, LCP-Tacro rapidly attained therapeutic blood levels.

The number of certain adverse events also was lower in the LCP-Tacro group.

| Adverse Events | LCP-Tacro (N = 268) | Prograf (N = 275) |
|---|---|---|
| Complications of transplanted kidney | 19 (7.1%) | 30 (10.9%) |
| Peripheral oedema | 42 (15.7%) | 57 (20.7%) |
| Diarrhea | 82 (30.6%) | 92 (33.5%) |
| Deep vein thrombosis | 0 (0%) | 6 (2.2%) |
| Constipation | 18.3% | 24.4% |
| Anemia | 26.1% | 28.7% |
| Low blood phosphate | 13.4% | 15.3% |
| Nausea | 13.1% | 14.9% |

All references, including published patent applications and patents, are hereby incorporated by reference.

The invention claimed is:

1. A method of suppressing organ rejection in a de novo African-American transplant patient comprising initiating oral treatment with a once-daily extended release tacrolimus dosage form at an initial dose of from about 0.15 to about 0.20 mg/kg/day following transplantation, wherein (i) the once-daily extended release tacrolimus dosage form provides a fluctuation of less than 100%, a swing less than 120%, or both, and (ii) the extended release dosage form releases at least 50% of the tacrolimus in the colon and/or the lower ileum.

2. The method of claim 1, wherein the patient has the CYP 3A5*1 genotype.

3. The method of claim 1, wherein dosing is initiated within 48 hours following transplantation.

4. The method of claim 1, wherein the extended release dosage form releases at least 50% of the tacrolimus in one or more of the colon ascendens, colon transversum and colon decendens.

5. The method of claim 1, wherein the extended release tacrolimus dosage form is administered once daily in the morning.

6. The method of claim 1, wherein the extended release tacrolimus dosage form is administered without food.

7. The method of claim 1, wherein the once-daily extended release tacrolimus dosage form provides a fluctuation of less than 100% and a swing less than 120%.

8. The method of claim 1, wherein the patient received a liver, kidney, or heart transplant.

9. The method of claim 1, wherein the dose of the extended release tacrolimus dosage form is not adjusted during the first 48 hours after the initial dose.

10. The method of claim 1, wherein the once-daily extended release tacrolimus formulation releases at most 63.5% of the tacrolimus in the dosage form at the 12 hours time point, when tested according to USP II dissolution test (paddle) method in 900 ml of an aqueous medium at pH 4.5 and comprising 0.005% hydroxypropylcellulose and 0.5% of the surfactant sodium lauryl sulfate, at 37° C.±0.5° C. and a paddle speed of 100 rpm.

11. The method of claim 1, further comprising adjusting the dose of the extended release tacrolimus dosage form so that the whole blood pre-dose (trough) concentration of tacrolimus is maintained in the range of from about 8.8 to about 9.3 ng/mL from day 2 to week 3 of tacrolimus treatment, and from about 6.5 to about 8.8 ng/mL for month 1 to 12.

12. A method of suppressing organ rejection in a de novo African-American organ transplant recipient, the method comprising
(a) initiating oral treatment with a once-daily extended release tacrolimus dosage form at an initial dose of from about 0.15 to about 0.20 mg/kg/day following transplantation, wherein
(i) the once-daily extended release tacrolimus formulation provides a fluctuation of less than 100%, a swing less than 120% or both; and
(ii) the once-daily extended release tacrolimus formulation releases the tacrolimus substantially in the colon and/or the lower ileum; and
(b) concomitantly treating the recipient with an IL-2 receptor antagonist and mycophenolate mofetil.

13. The method of claim 12, wherein the patient has the CYP 3A5*1 genotype.

14. The method of claim 12, wherein dosing is initiated within 48 hours following transplantation.

15. The method of claim 12, wherein the extended release dosage form releases at least 50% of the tacrolimus in one or more of the colon ascendens, colon transversum and colon decendens.

16. The method of claim 12, wherein the extended release tacrolimus dosage form is administered once daily in the morning.

17. The method of claim 12, wherein the extended release tacrolimus dosage form is administered without food.

18. The method of claim 12, wherein the once-daily extended release tacrolimus dosage form provides a fluctuation of less than 100% and a swing less than 120%.

19. The method of claim 12, wherein the patient received a liver, kidney, or heart transplant.

20. The method of claim 12, wherein the once-daily extended release tacrolimus formulation releases at most 63.5% of the tacrolimus in the dosage form at the 12 hours time point, when tested according to USP II dissolution test (paddle) method in 900 ml of an aqueous medium at pH 4.5 and comprising 0.005% hydroxypropylcellulose and 0.5% of the surfactant sodium lauryl sulfate, at 37° C.±0.5° C. and a paddle speed of 100 rpm.

* * * * *